United States Patent [19]

James et al.

[11] Patent Number: 5,080,784
[45] Date of Patent: Jan. 14, 1992

[54] SOLVENT MIXING DEVICE FOR LIQUID CHROMATOGRAPHY

[75] Inventors: Phillip A. James, Mepal; Martin A. Whitehead, Landbeach, both of England

[73] Assignee: U.S. Philips Corporation, New York, N.Y.

[21] Appl. No.: 520,994

[22] Filed: May 9, 1990

Related U.S. Application Data

[60] Continuation of Ser. No. 330,236, Mar. 29, 1989, abandoned, which is a division of Ser. No. 94,578, Sep. 9, 1987, Pat. No. 4,842,730.

[30] Foreign Application Priority Data

Sep. 17, 1986 [NL] Netherlands .................. 8622327

[51] Int. Cl.$^5$ .................................. B01D 15/08
[52] U.S. Cl. ........................... 210/198.2; 210/101; 366/165
[58] Field of Search ............... 366/165; 422/70; 210/101, 198.2, 96.1

[56] References Cited

U.S. PATENT DOCUMENTS

| | | | |
|---|---|---|---|
| 671,075 | 4/1901 | White | 366/165 |
| 895,795 | 8/1908 | Sampson | 366/165 |
| 2,528,094 | 10/1950 | Walker | 366/165 |
| 2,653,801 | 9/1953 | Fontein | 366/165 |
| 2,884,942 | 5/1959 | Caldwell | 366/165 |
| 3,291,456 | 12/1966 | Deane | 366/165 |
| 3,830,369 | 8/1974 | Pfadenhauer | 210/198.2 |
| 3,934,456 | 1/1976 | Munk | 210/198.2 |
| 3,994,480 | 11/1976 | Fothergill | 366/165 |
| 4,073,725 | 2/1978 | Takeuchi | 210/198.2 |
| 4,116,046 | 9/1978 | Stein | 210/198.2 |
| 4,230,630 | 10/1980 | Mag | 366/165 |
| 4,498,819 | 2/1985 | El-Saie | 366/165 |
| 4,595,496 | 6/1986 | Carson | 210/198.2 |
| 4,630,469 | 12/1986 | Bade | 210/198.2 |

FOREIGN PATENT DOCUMENTS

| | | | |
|---|---|---|---|
| 522772 | 3/1931 | Fed. Rep. of Germany | 366/165 |
| 611047 | 3/1935 | Fed. Rep. of Germany | 366/165 |
| 60-159646 | 8/1985 | Japan | 210/198.2 |
| 1419805 | 12/1975 | United Kingdom | 366/165 |
| 1439025 | 6/1976 | United Kingdom | 366/165 |

Primary Examiner—Ernest G. Therkorn
Attorney, Agent, or Firm—Paul R. Miller

[57] ABSTRACT

Liquid chromatography apparatus includes a solvent mixer which comprises a tapering or conical enclosed chamber (21) having an inlet (22) adjacent its larger end and an outlet tube (23) which extends through the base of the chamber (21) and has its open end adjacent to the apex (25) of the chamber. The mixing action takes place as the shape of the chamber (21) and position of the inlet (22) causes the liquid to shear in layers as it rotates up the chamber wall from the larger to the smaller end. The shear causes a good mixing action without requiring any movable devices within the chamber to stir the liquid.

4 Claims, 2 Drawing Sheets

SOLVENT MIXING DEVICE FOR LIQUID CHROMATOGRAPHY

This is a continuation of application Ser. No. 330,236, filed Mar. 29, 1989, now abandoned, which, in turn, is a division of Ser. No. 094,578, filed Sept. 9, 1987, now U.S. Pat. No. 4,842,730.

The invention relates to liquid chromatograph apparatus comprising a separating column, first means for feeding a selected one or combination of more than one of a plurality of solvents to the column, second means for injecting a sample into the solvent for delivery to the column, and a detector for detecting sample components in the output from the column, wherein the first means comprises a pump and a solvent mixer.

In liquid chromatography it is frequently desired to mix a number of solvents to perform what is known as gradient chromatography. In gradient chromatography a pre-defined change in the mobile phase or solvent strength is made to occur during a chromatographic analysis. The change in composition of the mobile phase is required when a single solvent mixture does not resolve the component in a sample mixture adequately within an exceptable time.

The changes in solvent composition are achieved by mixing solvents from two or more sources. This mixing can take place either at low pressure before the pump or at high pressure subsequent to the pump. In low pressure mixing a number of solvents are fed via switching valves to the inlet of the pump whereas in high pressure mixing each solvent is supplied through a pump and the outlet of each pump is at the working pressure of the column.

With either system a means is required of thoroughly mixing the components of the mobile phase before it is fed to the column clearly if several solvents are mixed together using switching valves a series of slugs of each component are supplied to the pump and these need to be mixed together to form the appropriate gradient of solvents. This mixing may take place either prior to or subsequent to the pump. Such mixers have typically comprised a chamber in which a stirrer has been provided with, the stirrer comprising a vane which is rotated magnetically by means of an externally generated magnetic field. However, these mixers tend to be complex and expensive.

It is an object of the invention to provide a liquid chromatograph in which solvent mixing is achieved more simply than in such prior chromatographs.

The invention provides a liquid chromatograph apparatus as set forth in the opening paragraph, characterised in that the solvent mixer comprises a tapering enclosed chamber, having an inlet located adjacent to its larger end and an outlet located adjacent to its smaller end.

The tapering chamber uses the liquid flow through the chamber to stir the liquid. The tapered shape of the chamber causes the liquid to shear in layers as it rotates up the chamber wall from the larger to the smaller end. This shear causes a good mixing action without requiring any movable devices within the chamber to stir the liquid.

The mixing chamber may be conically shaped with, the inlet being located adjacent to the base of the cone and the outlet adjacent to the apex of the cone. This enables a relatively simple manufacturing process to be used.

The cone may be a right circular cone and be arranged with its base horizontal and below the apex. This allows air bubbles to be purged from the system since they will rise to the top of the cone and be forced out of the chamber via the outlet by the flow of liquid.

The outlet may comprise a tube which passes through the larger end of the tapering enclosed chamber and extends within the chamber so that its open end is adjacent the smaller end of the chamber. The chamber may be frusto-conical. The inlet may comprise a tube which passes through the curved surface of the cone and which extends parallel to the base of the cone.

The invention further provides a solvent mixer for liquid chromatograph apparatus characterised in that the solvent mixer comprises a tapering enclosed chamber having an inlet located adjacent to its larger end and outlet located adjacent to its smaller end. The mixing chamber may be formed as a right circular cone with, the inlet being located adjacent to the base of the cone and the outlet comprising a tube which passes through the base of the cone and extends within the conical chamber so that its open end is adjacent the apex of the cone. The chamber may be frusto-conical.

BRIEF DESCRIPTION OF THE DRAWINGS

An embodiment of the invention will now be described, by way of example, with reference to the accompanying drawings, in which.

DESCRIPTION OF THE PREFERRED EMBODIMENTS

Figure 1:
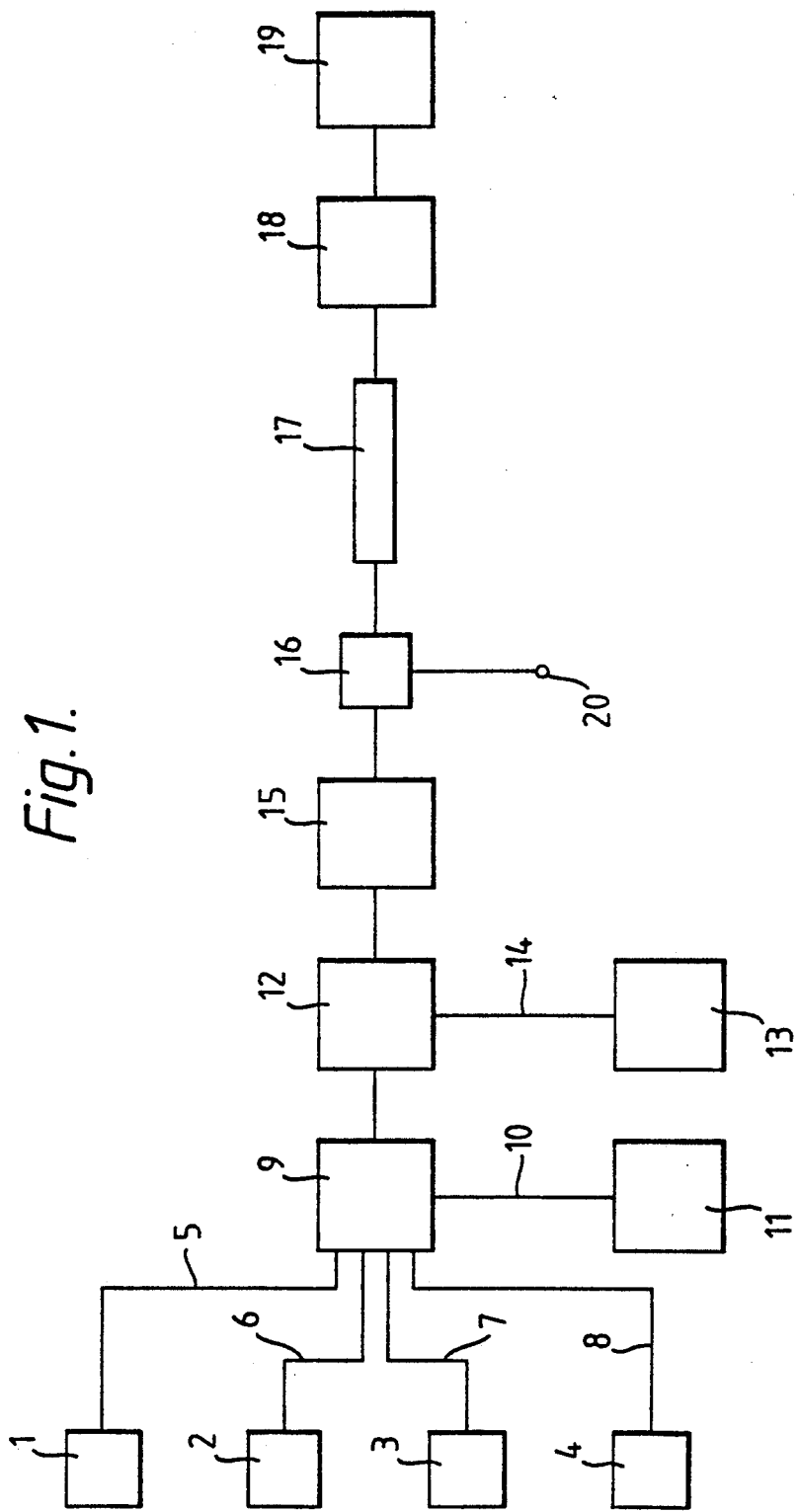
FIG. 1 shows in block schematic form a liquid chromatograph apparatus according to the invention.

The liquid chromatograph apparatus shown in FIG. 1, comprises four solvent reservoirs 1 to 4, which are fed via individual tubes 5 to 8 to the inputs of a proportioning valve arrangement 9. The proportioning valve arrangement is electrically operated and is controlled over a line 10 from a solvent proportioning control arrangement 11. The outlet of the proportioning valve arrangement 9 is fed to the inlet of a pump 12. The pump 12 is controlled by means of a pump control circuit 13 over a line 14. The outlet from the pump 12 is fed to the inlet of a solvent mixer 15 whose outlet feeds a sample injection means 16. The outlet of the sample injection means 16 is fed to the input of a separating column 17 whose outlet is fed to a detector 18. The ouput of the detector 18 is fed to a signal processing and display arangement 19. A second port of the sample injection means 16 is fed with the sample via a sample inlet 20.

In operation a selected solvent is fed to the pump 12 via the proportioning valve arrangement 9. The proportioning valve arrangement 9 selects each of the solvent sources 1 to 4 in proportion to the desired composition of the solvent to be fed to the pump, that is the solvent proportioning control arrangement operates the appropriate valves at the appropriate times to feed either a selected one of the solvents 1 to 4 or to feed in quick succession two or more solvents to the pump inlet to provide a mixture of two or more solvents to be fed to the column. The pump control circuit 13 controls the speed of the pump to obtain the desired flow rate of the solvent. In order to ensure that the various components of the solvent to be fed to the column are thoroughly solvent mixer comprises a tapering enclosed chamber having an inlet located adjacently its larger end and an outlet located adjacent to its smaller end and may take the form shown in FIGS. 2 and 3.

Figure 2:
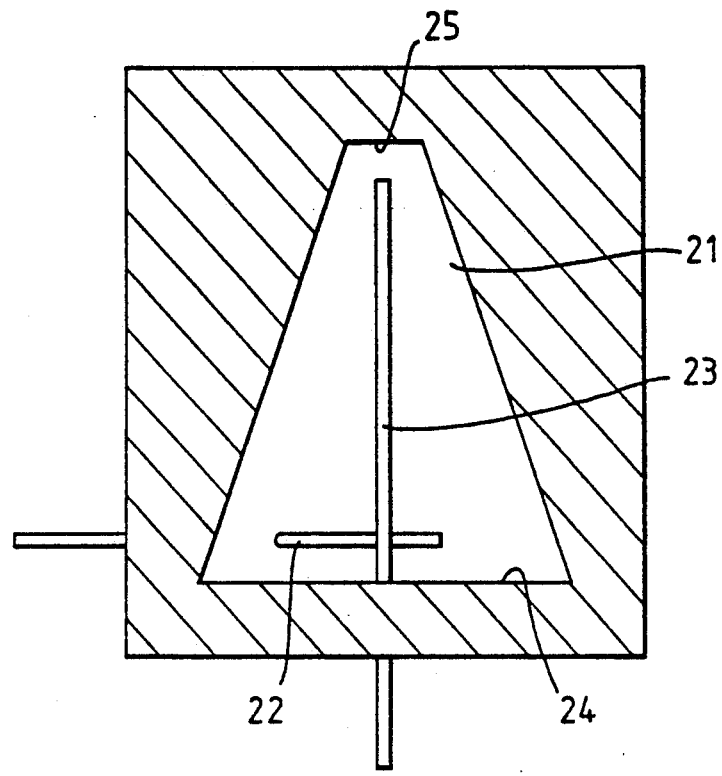
FIG. 2 is a cross-sectional view on line B-B of FIG. 3, of one embodiment of a solvent mixer according to the invention for use in the liquid chromatograph apparatus of FIG. 1.
Figure 3:
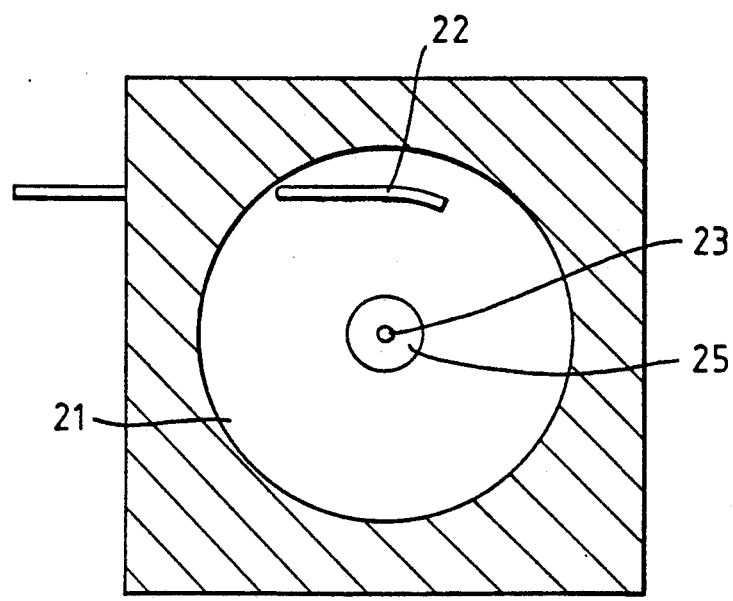
FIG. 3 is a cross-sectional view of the solvent mixer on line A-B of FIG. 2.

As shown in FIGS. 2 and 3 the solvent mixer comprises a frusto-conical chamber 21 having a inlet tube 22 which is arranged adjacent to the base of the cone and an outlet tube 23 whose open end is adjacent to the smaller end of the frusto-conical chamber 21. Liquid flowing into the chamber 21 through the inlet tube 22 will flow in a rotating fashion up the chamber wall and the shear forces between the rotating layers will cause the solvents to mix effectively as they travel up the chamber to the end of the outlet tube 23.

By arranging the conical chamber 21 so that the base 24 is horizontal and below the apex 25, easy removal of air when the system is being primed is obtained since air bubbles will rise to the top of the cone and then be forced down the outlet pipe 23. It is not essential that the conical chamber 21 is in fact frusto conical but a sharp upper point may allow air bubbles to become trapped without being flushed down the outlet pipe 23. Similarly the chamber need not be strictly conical, it merely requires a tapering profile from the inlet end to the outlet end. Hence, for example, a prismatic chamber would be acceptable under certain circumstances. However, it is preferable to avoid sharp corners since some of the solvent may become trapped in the corners and a certain amount of carry over of solvent components could occur. Consequently, a smoothly curved outer surface of the chamber is preferable. It is not necessary that the tapering surfaces taper linearly but it is mechanically convenient to form them in this way. As shown in FIG. 3 the inlet tube 22 has a curved portion adjacent to its end to cause the circular flow of liquid round the interior surface of the chamber 21 to start smoothly. However the inlet tube 22 may be a straight tube provided that it is positioned so that a circumferential liquid flow is produced.

From the outlet 23 of the mixing chamber 15 the solvents are fed to the sample injector 16 where a sample is injected into the solvent flow before the solvent and sample are fed to the column 17. The outlet of the column 17 is fed to a detector 18 which may be of any conventional design and the output of the detector is processed in a processing and display arrangement 19 and may be displayed by means of a chart recorder, plotter or video display unit. Alternatively, the detector output can be fed to a computer for analysis.

It is not essential that the solvent mixer is located after the pump but it is likely to be more effective if so located since the velocity of the liquid will be greater and a more effective mixing action will result.

We claim:

1. A solvent mixing device sized and dimensioned for chromatographic use comprising
   a circular, tapering enclosed chamber
   inlet means for feeding at least one of a plurality of solvents into said tapering enclosed chamber, said inlet means being disposed adjacent to a larger end of said tapering chamber, and
   outlet means for passing said solvents from said tapering enclosed chamber, said outlet means extending within said enclosed chamber from said larger end to an adjacent position to a smaller end of said tapering chamber to allow air to be forced down the outlet means, said smaller end being disposed above said larger end of said tapering chamber.

2. A solvent mixing chamber according to claim 1, wherein said tapering enclosed chamber is a right circular cone, wherein said inlet means is disposed adjacent to a base of said cone, and wherein said outlet means includes a tube extending through said base, said tube having an open end, said open end being in said adjacent position to said smaller end of said tapering enclosed chamber.

3. A solvent mixing chamber according to claim 1 or claim 2, wherein said tapering chamber is frusto-conical, said small end being a flat end of said tapering chamber.

4. A solvent mixing chamber according to claim 1 or claim 2, wherein said inlet means is disposed to create circumferential liquid flow of said at least one of said plurality of solvents upwardly in said chamber to said outlet means.

* * * * *